(12) United States Patent
Rockel et al.

(10) Patent No.: US 11,360,025 B2
(45) Date of Patent: Jun. 14, 2022

(54) AUTOMATED ANALYSIS TOOL FOR BIOLOGICAL SPECIMENS

(71) Applicant: Miltenyi Biotec GmbH, Bergisch Gladbach (DE)

(72) Inventors: Thomas Rockel, Düsseldorf (DE); Stefan Miltenyi, Bergisch Gladbach (DE); Sven Ignatius, Bergisch Gladbach (DE); Jurgen Krieg, Cologne (DE)

(73) Assignee: Miltenyi Biotec B.V. & CO. KG, Bergisch Gladbach (DE)

( * ) Notice: Subject to any disclaimer, the term of this patent is extended or adjusted under 35 U.S.C. 154(b) by 610 days.

(21) Appl. No.: 15/824,632

(22) Filed: Nov. 28, 2017

(65) Prior Publication Data

US 2018/0080876 A1   Mar. 22, 2018

Related U.S. Application Data

(63) Continuation-in-part of application No. 15/049,368, filed on Feb. 22, 2016, now abandoned.

(51) Int. Cl.
| | |
|---|---|
| *G01N 21/76* | (2006.01) |
| *G01N 21/25* | (2006.01) |
| *G01N 33/58* | (2006.01) |
| *G01N 21/64* | (2006.01) |
| *G01N 33/53* | (2006.01) |

(52) U.S. Cl.
CPC ....... *G01N 21/6428* (2013.01); *G01N 21/253* (2013.01); *G01N 21/6452* (2013.01); *G01N 21/6456* (2013.01); *G01N 21/6486* (2013.01); *G01N 21/76* (2013.01); *G01N 33/5302* (2013.01); *G01N 33/582* (2013.01); *G01N 21/6408* (2013.01); *G01N 2021/6432* (2013.01); *G01N 2201/061* (2013.01)

(58) Field of Classification Search
None
See application file for complete search history.

(56) References Cited

U.S. PATENT DOCUMENTS

| | | | | |
|---|---|---|---|---|
| 6,097,025 | A * | 8/2000 | Modlin | G01N 21/253 |
| | | | | 250/205 |
| 2005/0030601 | A1* | 2/2005 | Smith | G01N 21/6452 |
| | | | | 358/504 |
| 2012/0220022 | A1* | 8/2012 | Ehrlich | G01N 15/14 |
| | | | | 435/286.2 |

* cited by examiner

*Primary Examiner* — Neil N Turk
(74) *Attorney, Agent, or Firm* — Jaquelin K. Spong

(57) ABSTRACT

Systems and methods are described for analyzing a plurality of biological samples with a plurality of fluorescent reagents in an automated fashion. The system may include two optical systems, a fluorescence imaging system and an optical quenching system. These two systems may be placed laterally adjacent to one another, and generally beneath one of the wells of sample-containing microtiter plate. The biological sample contained therein may be stained with a series of fluorescent reagents, with the fluorescence quenched between stainings. By precise positioning of the sample with respect to the imaging system, the sample may be imaged with a plurality of serially applied reagents.

16 Claims, 10 Drawing Sheets

AUTOMATED ANALYSIS TOOL FOR BIOLOGICAL SPECIMENS

CROSS REFERENCE TO RELATED APPLICATIONS

This US patent application is a continuation-in-part, claiming priority to U.S. patent application Ser. No. 15/049,368, filed Feb. 22, 2016, and which is incorporated by reference herein in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a tool for analyzing biological specimens.

Fluorescent dyes conjugated to one or more antibodies are commonly used for immunofluorescence analysis. A vast number of variants in terms of antibodies, fluorescent dyes, flow cytometers, flow sorters, and fluorescence microscopes has been developed in the last two decades to enable specific detection and isolation of target cells.

Fluorochrome conjugates targeting the antigen of interest are used to detect and image cell structures of tissues. In these techniques, sequentially elimination of the fluorescence signal and re-staining allow a higher multiplexing potential compared to standard procedures using simultaneously labeling and detection. For example, U.S. Pat. No. 7,741,045 B2, EP 0810 428 B1 or DE10143757 disclose elimination of the fluorescence signal by photo- or chemical destruction of the conjugated fluorescent moieties.

In the aforementioned techniques, the resulting fluorescence signals are collected as an image. By sequentially elimination of the fluorescence signal and re-staining with different fluorochrome-conjugates, different antigens are detected, resulting in a plurality of images of the same specimen showing different parts (antigens) of the specimen. The quality of the information gathered with these techniques is highly dependent on the resolution of the images, the precision of the handling steps and the time required between steps, during which the sample is manipulated. The known techniques allow a very limited number of images of a particular biological sample through a series of stainings, due to the laborious handling steps. Accordingly, there is a need for an automated procedure for cycles of staining, imaging and elimination of the staining of biological specimens for analyzing proposes.

SUMMARY

Described here is a system that allows sequential analysis of a biological sample in situ, under computer control. The device allows the sequential application of a large number of fluorescent reagents to the same biological sample, and the observation of the sample through a transparent support by an imaging mechanism. The imaging mechanism may be a fluorescence imaging system which, in combination with a data-collecting computer, may form a visual image of the biological sample stained with a series of various reagents. Between each of the reagents, the fluorescence may be quenched by a second optical system disposed laterally adjacent to the fluorescence imaging system, which irradiates the sample with sufficient light to disable or destroy the fluorescing moiety.

Accordingly, the system may include a plurality of samples and a plurality of reagents, each contained in a separate well of a microtiter plate. An automated fluid handling system may be included, wherein a robotically controlled pipette retrieves a quantity of a particular reagent from one of the plurality of reagent vessels, and deposits that quantity into a particular sample well containing a particular biological sample.

The plurality of microtiter wells may be provided by a plastic, disposable microtiter plate, with the small fluidic wells formed therein. Each of the wells may contain different compounds, such as reagents, antigen recognizing moieties having detection moieties, such as antibodies with fluorescent dyes, antibiotics, biological nutrients, toxins, stains, oxidants. Alternatively, the disposable may comprise a plurality of functionalized, segmented areas wherein a biologically active structure is affixed.

Accordingly, the system may include a fluorescence system that measures a fluorescence signal, an aperture for holding a disposable containing at least one biological sample over the fluorescence system, a quenching system that provides quenching light to quench the fluorescence signal from the biological sample, a fluid handling system that supplies and/or removes fluids into and/or from the container, a mechanism for moving at least one of the aperture, the fluorescence system, the quenching unit and the fluid handling system in a least two orthogonal dimensions that define a working plane, and a control unit that executes a routine including excitation of the fluorescent dye, detection and collection of the fluorescence signals and quenching of the fluorescence signals in an automated fashion.

BRIEF DESCRIPTION OF THE DRAWINGS

Various exemplary details are described with reference to the following figures, wherein.

DETAILED DESCRIPTION

Figure 1:
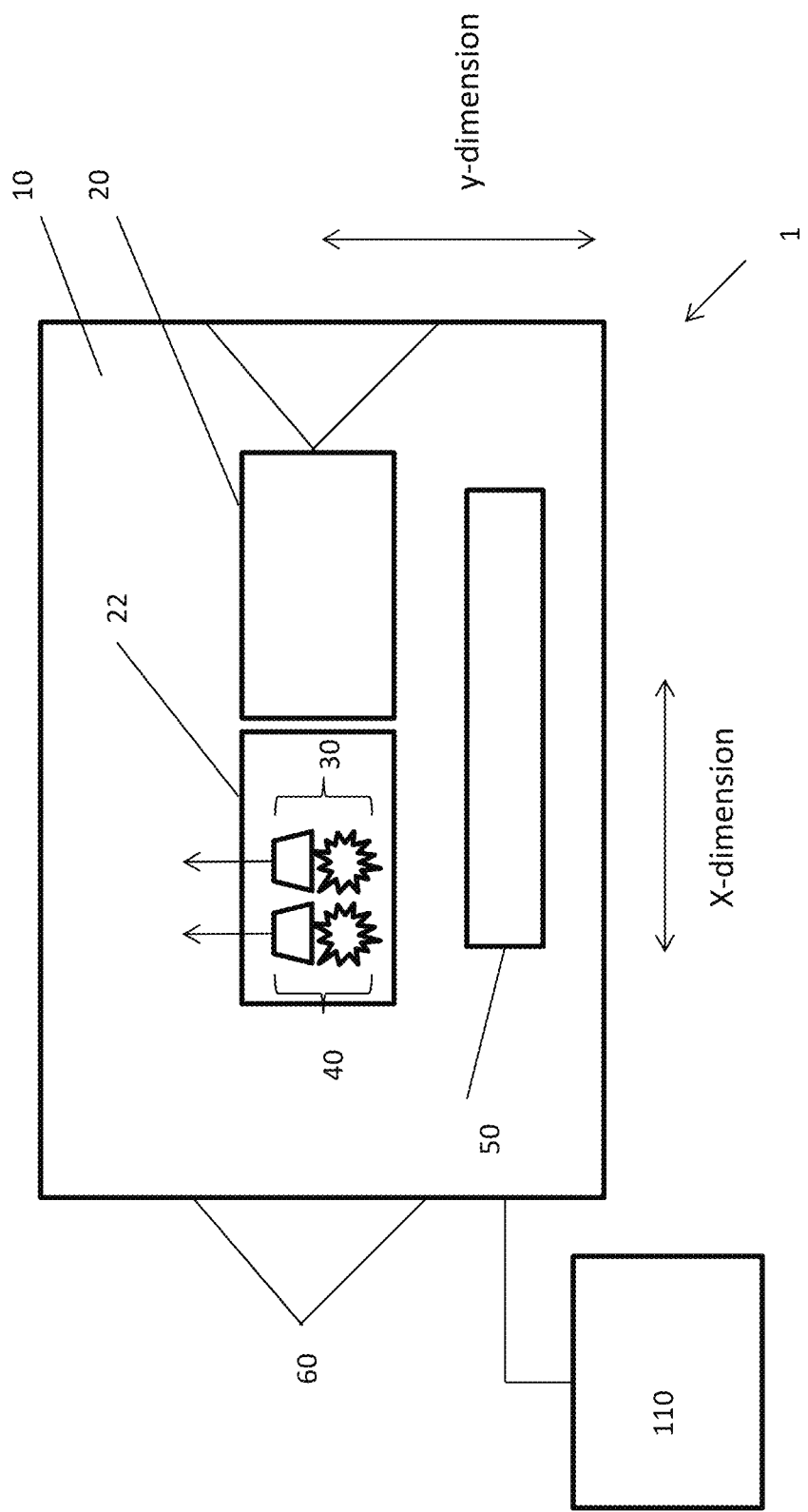
FIG. 1 is a simplified plan view of the automated analysis tool.

Systems and methods are described for analyzing a plurality of biological samples with a plurality of fluorescent reagents in an automated fashion. In the system, a robotically controlled pipetting system may retrieve a quantity of a fluorescent reagent from one of a plurality of fluid vessels, each holding a different reagent. The robotically controlled pipetting system may then deliver that quantity of reagent to a specific one of a plurality of sample-holding fluidic wells. The fluid sample wells may also contain a buffer fluid, as well as the biological sample. The plurality of reagents may be stored in the reagent vessels of a microtiter plate 90, whereas the plurality of samples may be stored in the sample wells of microtiter plate 92. Accordingly, as used herein, reference number 90 refers to a disposable microtiter plate storing reagents in vessels, and reference number 92 designates a disposable microtiter plate storing separate biological samples in wells.

Fluorescent Reagents

The fluorescent reagents used in the present invention comprise a fluorescent moiety and an antigen recognizing moiety, optionally connected by a spacer molecule.

Suitable fluorescent moieties are those known from the art of immunofluorescence technologies, e.g., flow cytometry or fluorescence microscopy. Useful fluorescent moieties might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, or metallo-organic complexes, such as Ru, Eu, Pt complexes. Besides single molecule entities, clusters of fluorescent proteins or small organic molecule dyes, as well as nanoparticles, such as quantum dots, upconverting nanoparticles, gold nanoparticles, dyed polymer nanoparticles can also be used as fluorescent moieties.

The fluorescent moiety can be covalently or non-covalently coupled to the antigen recognizing moiety, via an optional spacer. Methods for covalently or non-covalently conjugation are known by persons skilled in the art. In case of a covalent bound between the fluorescent moiety, the antigen recognizing moiety or the optional spacer, a direct reaction of an activated group on one of the fluorescent moiety, the antigen recognizing moiety or the spacer with an functional group on the respective other units may be used.

Antigen Recognizing Moiety

The term "antigen recognizing moiety" refers to any kind of antibody or fragmented antibody or fragmented antibody derivatives, directed against markers expressed on the cells of the cell sample. The term relates to fully intact antibodies, fragmented antibody or fragmented antibody derivatives, e.g., Fab, Fab', F(ab')2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificial engineered binding molecules, e.g., peptides or aptamers which target, e.g., cell surface molecules.

The fluorescent reagents used in the method of the invention may comprise up to 100, preferably 1-20 antigen recognizing moieties and/or detection moieties.

Preferably, fluorescent reagents used in the present invention comprise a fluorescent moiety and an antibody directed against antigen expressed by the biological specimens (target cells) intracellular, like IL2, FoxP3, CD154, or extracellular, like CD3, CD14, CD4, CD8, CD25, CD34, CD56, and CD133.

Biological Samples

The biological samples comprise target moiety which can be detected/recognized by the antigen recognizing moieties of the fluorescent reagents. Biological samples may originate from any specimen, like whole animals, organs, tissues slices, cell aggregates, or single cells of invertebrates, (e.g., *Caenorhabditis elegans, Drosophila melanogaster*), vertebrates (e.g., *Danio rerio, Xenopus laevis*) and mammalians (e.g., *Mus musculus, Homo sapiens*). A biological sample may have the form of a tissues slice, cell aggregate, suspension cells, or adherent cells. The cells may be living or dead. These reagents may each be contained in a separate fluid vessel, such that each fluid vessel contains at least one of reagents, antigen recognizing moieties having detection moieties, antibodies with fluorescent dyes, antibiotics, biological nutrients, toxins, stains, and oxidants. Each of the reagents may be retrieved by the fluid handling system and applied to the biological sample being imaged by the system, as will be described further below.

Fluorescence System

Fluorescence excitation is performed via irradiation of light of proper wavelength usually in the visible spectral range, e.g. green light of 520-560 nm for the excitation of R-phycoerythrin (R-PE). The excitation unit therefore provides electromagnetic radiation in the spectral range where the specific fluorophore absorbs. The fluorophore then emits the fluorescence light of red-shifted wavelength (shifts are typically around 20 nm) which can be detected separately from the excitation radiation. Typical implementations of fluorescence microscope excitation units harbor a white light source such as arc lamps, xenon or metal halide lamps and successive filters to generate the spectral band required for the excitation. Also lasers or light emitting diodes are used.

Quenching Unit

The quenching unit may provide a high intensity irradiation of the sample using light of a wavelength which is absorbed by the specific fluorophore. For a lot of commonly used dyes, a combination of blue (450-500 nm), green (520-560 nm) and red (630-650 nm) generating LEDs is sufficient. Higher intensity of the radiation reduces the time needed for the quenching. Using about 300 mW/cm$^2$ for PE, a half-life time of the exponential decay of the fluorescence signal of roughly 30 seconds is obtained. A reduction in fluorescence signal to 1-5% of the starting signal therefore needs about three minutes. This can be done simultaneously for different fluorophores, eg FITC (excitation 470 nm, emission 520 nm), R-PE (ex 530 nm, em 580 nm), APC (ex 630 nm, em 660 nm). In this embodiment, the quenching unit can also be the same component as the excitation unit.

In another variant of the invention, the quenching unit provides chemicals which eliminate the fluorescence dye for example by oxidative bleaching. The necessary chemicals for bleaching are known from the above-mentioned publications on "Multi Epitope Ligand Cartography", "Chip-based Cytometry" or "Multioymx" technologies.

In yet another variant of the invention, the fluorescence dye comprises an enzymatically degradable spacer. To eliminate the fluorescence emission, the quenching unit may provide appropriate enzymes which degrade the spacer, thereby releasing the dye from biological sample. The released dye can be removed from the sample by washing. Suitable fluorescence dyes and enzymes are disclosed in EP patent application EP15200338.0 and include, for example, polysaccharides, proteins, peptides, depsipeptides, polyesters, nucleic acids, dextrans, pullulans, inulins, amylose, cellulose, hemicelluloses, xylan, glucomannan, pectin, chitosan, or chitin as encymatically spacer and hydrolases, lyases or reductases as enzyme. The fluid handling system, as described below, may provide at least one of fluorescence dyes, compounds quenching the fluorescence signals, whashing fluids and/or buffer to the biological sample.

Method of the Invention

The system of the invention enables the detection, location and imaging of target moieties like antigens on the biological specimens recognized by the fluorescent reagents. With the system of the invention, cells can be immobilized and then contacted with the fluorescent reagents. The antibodies are recognized by the respective antigens on the biological specimen (for example on a cell surface) and after removing the unbound fluorescent reagent and exciting the fluorescent moieties, the location of the antigen is detected by the fluorescence emission of the fluorescent reagent.

The location of the target moieties is achieved by a digital imaging device with a sufficient resolution and sensitivity for the wavelength of the fluorescence radiation. The digital imaging device may be used with or without optical enlargement for example with a fluorescence microscope. The resulting images are stored on an appropriate storing device like a hard drive, for example in RAW, TIF, JPEG, or HDF5 format.

In order to detect different antigens, different fluorescent reagents comprising different antigen recognizing moieties having the same or a different fluorescent moiety are provided. Since the parallel detection of fluorescence emission with different wavelengths is limited, the fluorescent reagent are utilized sequentially individually or in small groups (2-10) after the other. In this variant, an appropriate number of detectors may be utilized. Preferably, only one detector is used to detect the fluorescence emission of the various fluorescence reagents subsequently by masking all but one fluorescence emission with a filter.

In a variant of the invention, the biological specimens—especially suspensions of cells—of the sample are immobilized by trapping in microcavities or by adherence.

In general, the method of the invention can be performed in several variants. For example, the conjugate not recognized by a target moiety can be removed by washing for example with buffer before the target moiety labelled with the fluorescent reagent is detected.

In a variant of the invention, at least two fluorescent reagents are provided simultaneously or in subsequent staining sequences, wherein each antigen recognizing moiety recognizes different antigens.

The elimination of the fluorescence emission can be monitored in order to optimize process time. In the present invention, elimination of fluorescence emission is achieved when the fluorescence emission is reduced to less than 5%, preferably less than 1% of the starting fluorescence emission. For convenience, the elimination of fluorescence may be measured at the wavelength of the highest emission, but calculating the integral of the emission spectra is also suitable. In the variant of providing simultaneously more than one fluorescent reagent, the reduction of fluorescence emission is based on each of the fluorescence emission measured.

The systems and methods may also include two optical systems, a fluorescence imaging system 30 and an optical quenching system 40. These two systems may be placed laterally adjacent to one another, and generally beneath one of the wells of sample-containing microtiter plate 92. In other words, the light source of the quenching unit may be disposed laterally adjacent to the fluorescence system. Alternatively, the quenching unit may be disposed above the working plane. The microtiter plates 90 and 92 may be placed in the apertures of a movable stage 10, which moves the wells relative to either the fluid handling system 70 or the optical systems 30 and 40.

It should be understood, however, that embodiments of the invention may include systems wherein the sample may be moved relative to the optical systems 30 and 40, as well as embodiments wherein the optical systems 30 and 40 may be moved relative to the samples. For clarity of explanation, the invention is described with respect to an embodiment depicted in FIGS. 1-9 wherein the samples are moved on a movable stage 10, relative to the imaging system 30 and quenching system 40. It should be understood that alternative embodiments are also envisioned, wherein for example, the optical systems are moved relative to the biological samples. Accordingly, the apparatus may include a mechanism for moving at least one of the aperture and the fluorescence system in a least two orthogonal dimensions to image the biological samples.

FIG. 1 is a plan view of one embodiment of an automated analysis tool for biological specimens, 1. Included in the tool is a movable stage 10 into which two apertures 20 and 22 are formed. The movable stage 10 may be made of any rigid material which is lightweight and easy to machine such as aluminum. Not shown in FIG. 1 are a plurality of motors, such as stepper motors for example, which adjust the positioning of movable stage 10 in the two orthogonal directions shown. These two orthogonal directions, labeled the X direction and the Y direction in FIG. 1, define a movable x-y plane for the automated analysis tool 1. This plane is herein referred to as the working plane. The movable stage 10 may be moved in the x-y working plane under the control of a microprocessor, control unit or computer 110. The computer, or control unit 110, may move the aperture 20 or 22 in the working plane with a precision of +/− about 1 to 200 microns in the x or y direction, depending on the speed and precision required.

Also shown in FIG. 1 is a refrigeration unit, 50, which provides refrigeration for the biological specimen, the buffer, as well as the material of the movable stage 10, itself. Accordingly, the system may further comprise a cooling unit that cools the working plane and including the biological sample. Also shown in FIG. 1 is a chilled enclosure like an insulated box or a tent, 60, which may be placed over the two apertures 20, and 22 as well as the refrigeration unit, 50. The chilled enclosure may be formed as a tent of any minimally porous, flexible material such as a transparent mylar. The enclosure may be placed over apertures 20 and 22, to keep the chilled are in the environment around the biological sample, as described below. Accordingly, the automated system may further comprise a temperate control unit that controls the temperature of the biological sample to a set point between about 10-40° C.

Directly beneath the apertures 20, 22 may be two optical systems, 30 and 40. These two optical systems may be, respectively, a fluorescence imaging system, 30, and a florescence bleaching system, 40. The details of these two optical systems the fluorescence imaging system 30 and the florescence bleaching system 40, will be described further below. The optical systems 30 and 40 sit generally beneath at least one of aperture 20 or 22. For the purposes of illustration, these apertures are empty in FIG. 1, but when the analysis tool is in operation, the apertures 20 and 22 may hold biological specimen samples (in 22) and a collection of reagents (in 20), or vice versa, as will be described next. Not shown in FIG. 1 are the additional structures required for the optical imaging system 30 or fluorescence bleaching system 40. These additional structures may include additional lenses, mirrors, detectors, sources, and other optical components. These additional structures will be discussed further below.

The terms "quenching" and "bleaching" are used interchangeably herein, and should be understood to mean the diminution of fluorescence from a tagged biological sample, as a result of the chemical or radiative alteration of the fluorophore or its attachment to the tagged biological sample. Accordingly, the quenching system may further comprise a source of at least one of a chemical or radiation which alters a fluorescence capability of the reagent or its attachment to the biological sample.

It should be noted that the florescence imaging system 30 may be disposed directly adjacent to the florescence bleaching system 40.

Not shown in FIG. 1 are the stepper motors, gears, bearings, and other mechanical parts used to achieve repeatable, precise motion of the movable stage 10 in the x-y plane. Such components are readily available, and appropriate dimensions and other mechanical characteristics will depend on the details of the application. Also not shown are various damping mechanisms such as springs, dashpots and rubber bumpers. Such components may be used to isolate the automated analysis tool 1 from ambient, environmental factors like shock and vibration.

Figure 2:
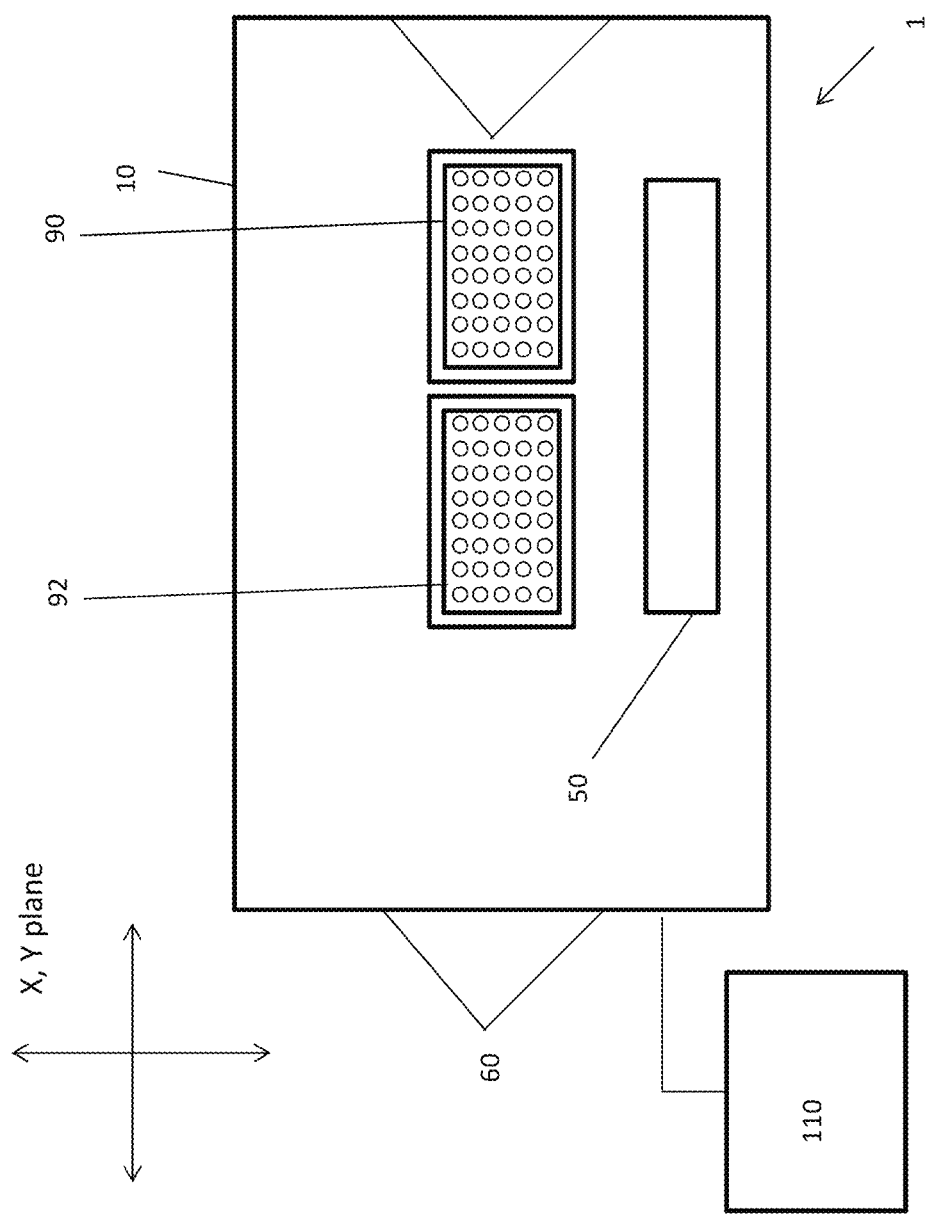
FIG. 2 is simplified side view of the automated analysis tool with a disposable sample holder disposed therein.

FIG. 2 is a plan view of automated analysis tool for biological specimens 1, with disposable sample holders 90 and 92 installed in apertures 20 and 22. As mentioned previously, in the description which follows, microtiter plate 90 may contain the reagents and microtiter plate 92 may contain the samples. Disposable sample holders 90 and 92 may be a rigid plastic structure of known dimension into which a plurality of fluid wells may be formed. Indeed, disposables 90 and 92 may both be multiwell titer plates having a standard form factor, with, for example, 96 small fluid wells formed therein.

The disposables 90 and 92 may alternatively be glass slides on which the biological sample is immobilized. In other embodiments, disposables 90 and 92 may include functionalized surfaces in distinct, separate regions on a transparent support such as plastic. The support may be a glass slide, or any other transparent surface which can hold the biological specimen and be imaged by fluorescence imaging system 30 and/or the fluorescence quenching system 40. The disposable may further comprise transparent and nontransparent parts wherein the biological sample is located on the transparent part, and the nontransparent parts either reflect or absorb light. Accordingly, the biological sample may be located on the transparent part and the nontransparent parts either reflect or absorb the fluorescence signals.

The material of the disposables 90 and 92 may be selected or coated to reduce light absorption. Opaque or optically absorptive materials may be chosen or transparent materials may be coated with reflective films using, for example, CVD (chemical vapour deposition) of metals or $TiO_2$ (reflection rather than absorption).

The movable stage 10 may be moved to adjust the precise positioning of a single well of disposable 92 or 92 relative to the other components. For example, disposable 92 may be located directly above the fluorescence imaging system 30 and/or the fluorescence quenching system 40, during sample manipulation. At other times, disposable 90 may be located directly below a liquid handling system, shown as pipette 70 during reagent retrieval, as will be described below with respect to FIG. 3. During sample manipulation, the movable stage may move to locate a particular sample well above the optical apparatus, either above the fluorescence imaging system 30 or above the fluorescence quenching system 40. Indeed, disposable 92 may be positioned such that a microscopic image of the contents of any of the wells in multiwell titer plate 90 or 92 may be imaged with precision.

As used herein, the terms "multiwell titerplate" and "microtiter plate" are used interchangeably, and both should be understood to mean a structure containing a plurality of small wells or depression, each of which may be used to hold a liquid or a specimen, separate from the other wells or depressions. Both refer especially to devices according to ANSI SBS 1-2004. "The "fluid handling system" may be a system capable of transferring fluids between fluid receptables. The fluid handling system may include a plurality of fluid vessels which hold a plurality of reagents, and a source of pneumatic pressure or vacuum, such that fluids can be withdrawn from at least one container and inserted into another." The "quenching unit" may be a source of a chemical or a source of electromagnetic radiation, which when applied to the biological sample, substantially diminishes the fluorescent light emitted by the biological sample.

Accordingly, the system may include a fluorescence system that measures a fluorescence signal, an aperture for holding a disposable containing at least one biological sample over the fluorescence system, a quenching system that provides quenching light to quench the fluorescence signal from the biological sample, a fluid handling system that may supply and/or remove a fluid into and/or from the container, a mechanism for moving at least one of the aperture, the fluorescence system, the quenching unit and the fluid handling system in a least two orthogonal dimensions that define a working plane, and a control unit that executes a routine including excitation of the fluorescent dye, detection and collection of the fluorescence signals and quenching of the fluorescence signals in an automated fashion.

Similar to FIG. 1, refrigeration unit 50 may cool the multiwell titerplates 90 and 92, as well as the fluids held therein. A substantially non-porous enclosure like a tent 60 may restrict the movement of air into the surrounding environment, thereby helping to keep the biological specimen in multiwell titerplates 90 or 92 cool.

Figure 3:
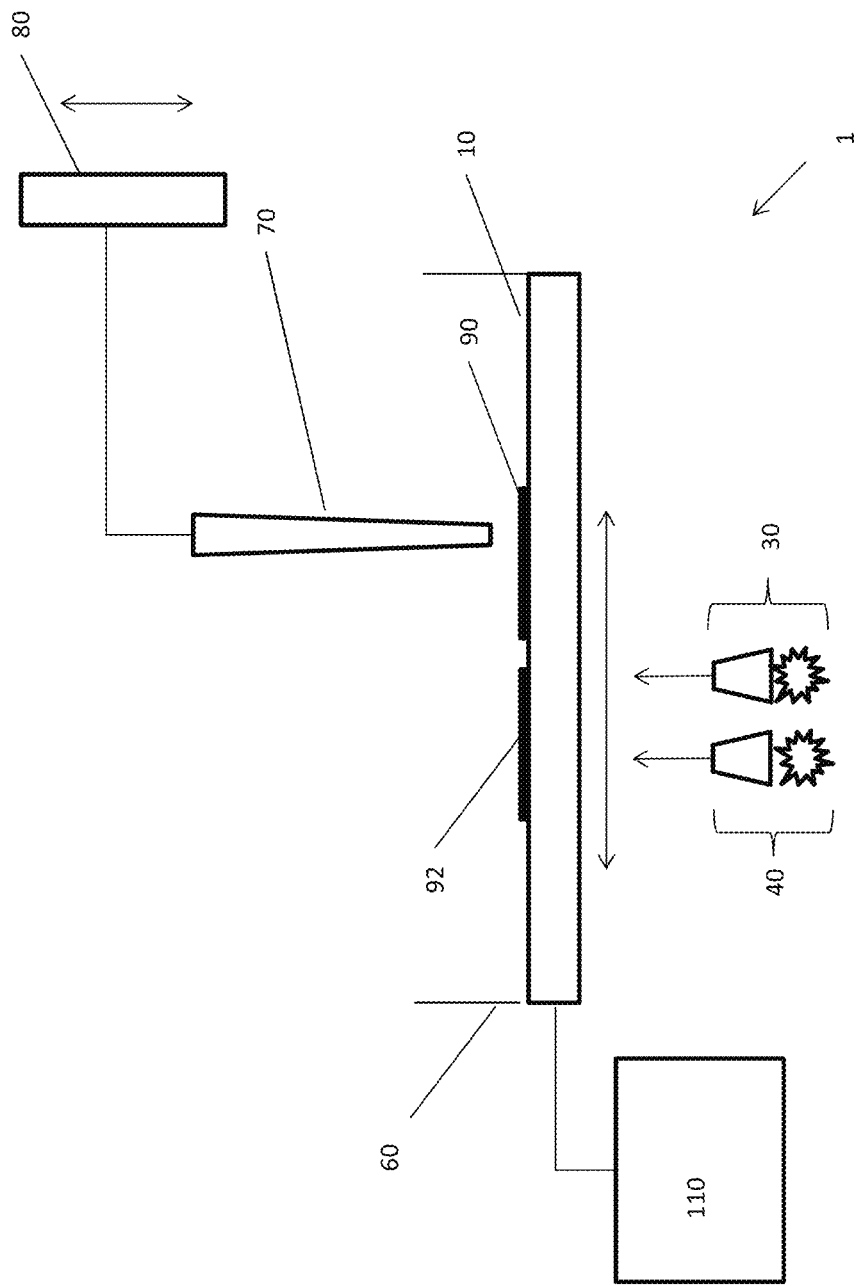
FIG. 3 is simplified side view of the automated analysis tool showing an automated pipetting system.

FIG. 3 as a side view showing the movable stage 10, and a manipulable pipette 70 held directly above multiwell titerplate 90. Pipette 70 may be held and controlled by position controller, pipette stage 80, and moved under the direction of a microprocessor or computer. Pipette stage 80 may move pipette 70 in the Z direction into any of the plurality of titer wells in microtiter plate 90. Each of the plurality of wells may contain different compounds and may include at least one of reagents, antigen recognizing moieties having detection moieties, antibodies with fluorescent dyes, antibiotics, biological nutrients, toxins, stains, oxidants. The pipette 70 may therefore be a robotically controlled pipette system disposed on a stage, wherein the pipetting system is movable along a z-axis orthogonal to the working plane, and is configured to apply different compounds to the biological sample.

Because movable stage 10 is movable in the X- and the Y-directions, only the Z direction motion is necessary for pipette 70 to retrieve any of the reagents held in any of the vessels of multiwell titerplate 90. Upon retrieval of a particular reagent, movable stage 10 is shifted and positioned such that the desired or appropriate well in multiwell titerplate 90 is positioned directly under pipette 70. Then pipe at 70 is lowered into the particular well of multiwell titerplate 90 and the reagent is deposited in the appropriate well of multiwell titerplate 90.

Accordingly, to stain a particular specimen with a particular reagent, the movable stage 10 maybe moved to position the particular well in multiwell titerplate 90 directly under pipette 70. Controller 80 then lowers pipette 70 into the fluid reagent held in the designated well of multiwell titerplate 90. Pipette stage 80 may cause suction to be applied to the head of pipette 70, in order to draw a predetermined volume of the fluid held in the well of microtiter plate 90. Pipette 70 is then withdrawn from the well.

Microprocessor 110 may then shift the movable stage 10 into a position where the desired or appropriate specimen that is contained in a particular well on multiwell titerplate 92 is positioned directly under pipette 70. Pipette 70 is then lowered into the well by controller 80. Pressure is applied to the head of pipette 70 to expel the contents of the pipette 70 into the designated well of microtiter plate 92 holding the biological specimen. The now-stained specimen may then be incubated. After incubation, the stained biological specimen may be imaged as described below.

Figure 4:
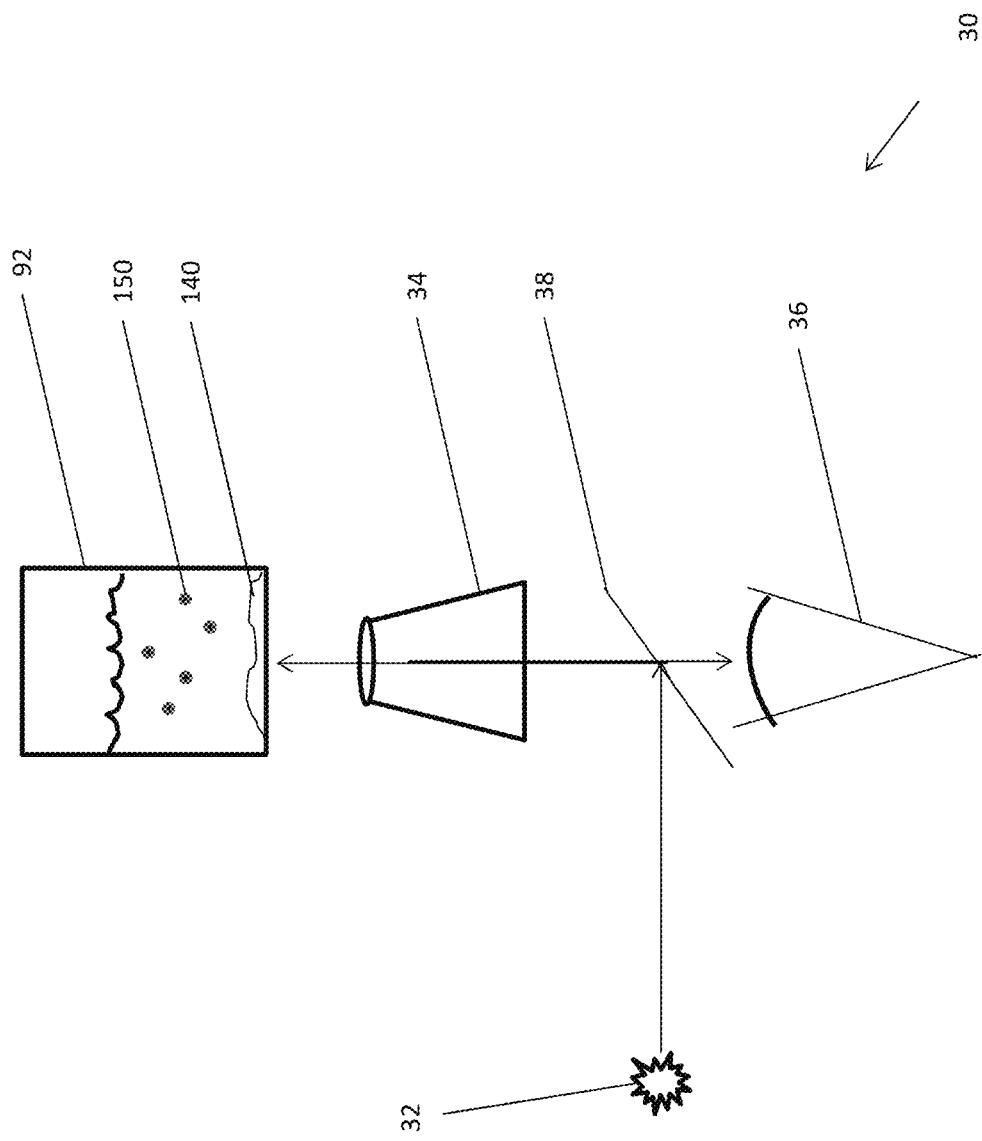
FIG. 4 is simplified side view of a fluorescence imaging system.

FIG. 4 is a conceptual view of the fluorescence imaging system 30. Fluorescence imaging 30 may include an optical light source 32, such as an LED source, which generates radiation in a band of wavelengths. This radiation may impinge upon a dichroic mirror 38 which reflects the radiation into an objective lens 34. The objective lens 34 may shape, focus or collimate the light. The radiation then impinges on a particular well of the microtiter plate 92. The multiwell titerplate well 92 may include a buffer fluid 150 and a biological specimen 140. Depending on the nature of the biological specimen 140, it may adhere to the bottom of the well in multiwell titerplate 92, or it may be floating or suspended in the buffer fluid 150.

If the biological specimen 140 is a cell, for example, it may have been combined with a stain or reagent. The stain or reagent may be a fluorophore conjugated with an antibody. The antibody may bind with a surface marker, or antigen, found on the membrane of the cell, and the fluorophore may emit a fluorescent photon upon irradiation by light of the proper wavelength. Accordingly, the light source 32 may emit light of this wavelength to excite the fluorophore which may then emit a fluorescent photon. The dichroic mirror 38 may reflect the radiation from the light source onto the tagged biological specimen 140, but the dichroic mirror 38 may transmit the fluorescent photon into the detector 36 as shown in FIG. 4.

Accordingly, dichroic mirror 38 may be engineered to reflect light at the wavelength of the laser or the optical source 32, but to transmit radiation at the wavelength of the florescence emitted from the biological sample 140. Optical detector 36 may be any pixelated, digital detector such as it CCD camera or micro channel plate. Objective lens 34 maybe movable or adjustable in the z-axis, so as to focus the appropriate spot on biological specimen 140 onto detector 36. The control unit xx may collect the fluorescence signals as images of the biological sample stained with a fluorescence dye.

Figure 5:
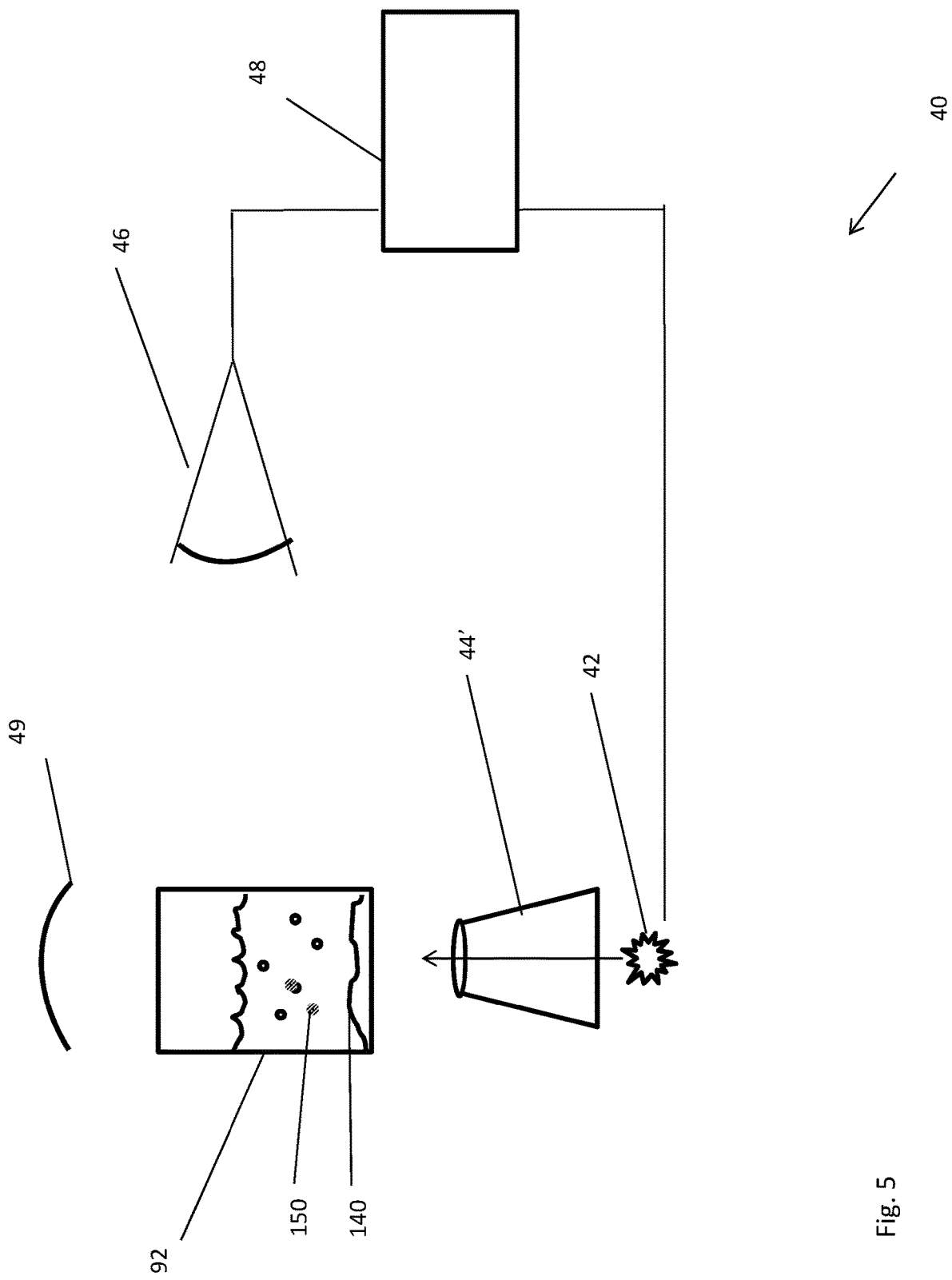
FIG. 5 is simplified side view of an optical quenching system with feedback control.

FIG. 5 is a conceptual side view of the fluorescence quenching system 40. Included in florescence quenching system 40 may be an optical source 42 which is focused by an objective lens 44 onto the biological specimen 140. As before, the biological specimen may be submerged in a buffer fluid 150 in a well in multiwell titerplate 92.

Optical source 42 may be an LED or laser, but in any case the wavelength of the emitted radiation is chosen to overlap an absorption band of the florescence moiety or tag affixed to the biological specimen 140. Upon application of this radiation, the biological specimen 140 with the affixed tag may have the fluorescent tag decomposed, dissociate, or destroyed by the radiation. Accordingly, the quenching system 40 may comprise an optical quenching system, which destroys the fluorescence of the reagent by illumination to light, and comprises an LED light source and an objective lens.

In any event, the fluorescent tag affixed to the biological sample 140 may cease to fluoresce in whole or in part. As a result, fluorescence emitted from the biological sample 140 in the multiwell titerplate 92 will be diminished. This reduced florescence may be detected by another optical detector 46 whose output is coupled to a computer 48.

Computer 48 may generate a signal which controls the amplitude of the radiation source 42. Optical detector 46 may be of the same type, or different, that optical detector 36. Accordingly, optical detector 46 may be any pixelated, digital detector such as it CCD camera or micro channel plate.

Accordingly, the quenching system may include a fluorescence detector which monitors the decay of the fluorescence signal of the reagent by illumination to light, as quenching data. The control unit may control the quenching system with a feedback loop based on the quenching data. Accordingly, the control unit may direct the quenching system to continue to apply the quenching radiation until a predefined fluorescent threshold is reached.

Upon detecting continued fluorescence from the biological specimen 140, as measured by detector 46, the computer 48 will increase or continue the current applied to optical light source 42 to increase or continue the amount of radiation applied to the biological specimen 140. Only when all of the fluorescent radiation ceases to be emitted from the biological specimen 140 or drops below some predetermined threshold value, the computer 48 may discontinue the driving signal to the optical light source 42. Accordingly, in some embodiments, the fluorescent quenching system 40 may have computer-controlled feedback mechanism, which determines when the quenching process of illumination the biological sample 140 may be discontinued.

Another element in fluorescent quenching system 40 may be a reflector 49 which may be disposed above the microtiter plate 92. Reflector 49 may reflect the quenching radiation emitted from the optical source 42 back through the biological specimen 140. By having the radiation pass an additional time, the quenching of the fluorescent signal may be more effective or efficient. Accordingly, the quenching system may further comprise at least one mirror which reflects a parts of the quenching radiation which is not absorbed by the biological sample, or the fluorescent dye, back into the biological sample.

As mentioned previously, in the embodiments described here, the stage 10 is moved in the working x-y plane to position a particular spot or feature of the biological specimen 140 in the imaging area of the fluorescent imaging system 30. Similarly, the spot or feature is then positioned above fluorescent quenching system 40 by moving the movable stage 10 in the x-y working plane. It should be understood however, that this is exemplary only, and that the optical systems 30 and 40 may alternatively be moved relative to the biological specimen 140. In other words, rather than positioning the x-y working plane with respect to the fluorescence imaging system 30 and fluorescence quenching system 40, the fluorescence imaging system 30 and fluorescence quenching system 40 may be positioned with respect to the biological specimen 140.

Figure 6:
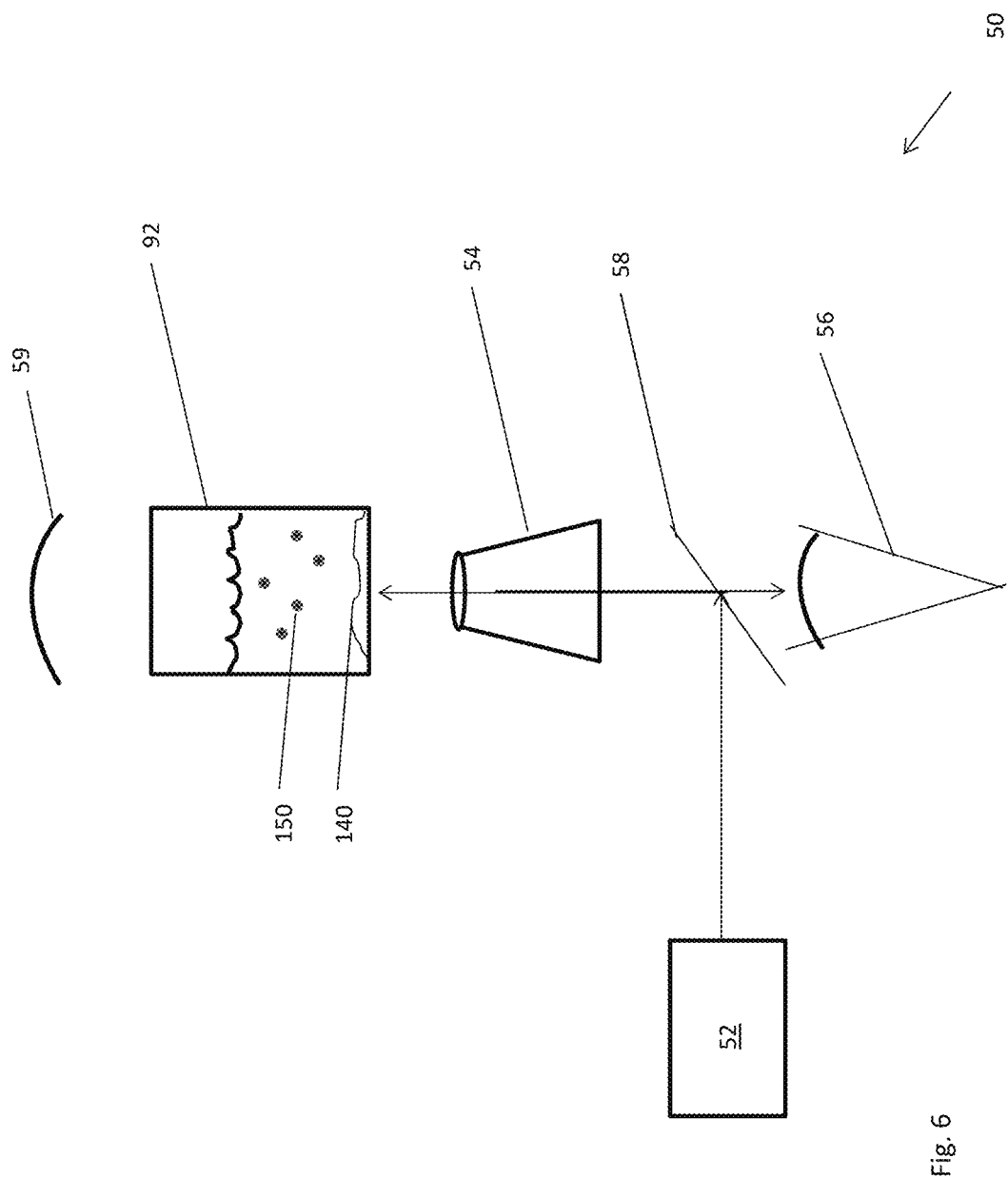
FIG. 6 is simplified side view of an optical quenching system with laser source and resonator mirror.

FIG. 6 is a conceptual view of another embodiment of the fluorescence quenching system 50. In contrast to fluorescence quenching system 40, in fluorescence quenching system 50 optical source 42 maybe a coherent source such as a laser 52. The laser 52 may emit light at a specific wavelength, or narrow band of wavelengths. As before with respect to FIG. 5, the radiation may be reflected from a dichroic mirror 58 and through an objective lens 54 onto the biological specimen 140. This radiation may then be reflected by the additional reflector disposed above multiwell titerplate 92. This optical reflector 59 may then reflect the laser radiation back through the biological specimen 140 for a second pass. As with optical reflector 49, this may increase the effectiveness of the optical quenching of the fluorescent signal. However, in the laser embodiment of FIG. 6, the mirrors 59 and dichroic mirror 58 may form a resonant cavity and amplify the laser radiation emitted by laser source 52. As before, the resonant cavity may enhance the effectiveness of the radiation source 42, by providing multiple passes of the radiation to the sample on substantially the same spot.

Figure 7:
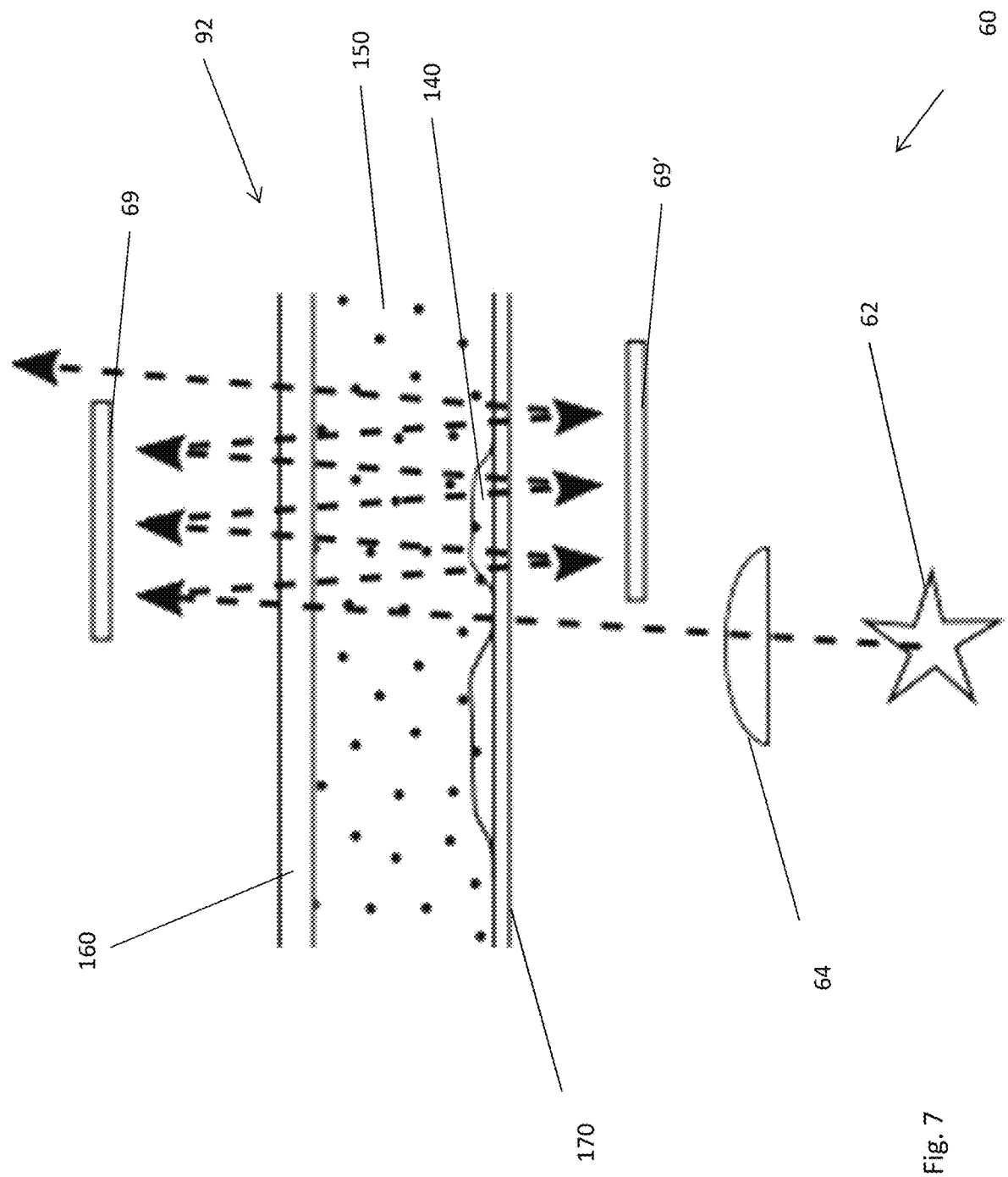
FIG. 7 simplified side view of an embodiment of an optical quenching system with multiple passes through the biological sample.

FIG. 7 is a conceptual side view of another embodiment of the optical quenching system 60. And optical quenching system 60, once again a source of radiation 62 is focused through an objective lens 64 and into the multiwell titerplate 90. Optical source 62 may be either a light emitting diode (LED 42 as in FIG. 4) or laser (Laser source 52 as in FIG. 5). When entering the multiwell titerplate 92, the radiation may pass through a transparent, glass base support 170 of multiwell titerplate 92. This transparent base 170 may support a biological specimen 140. Biological specimen 140 may be at the bottom of particular well of multiwell titerplate 92, but submerged in a fluid such as a buffer fluid 150. At the top of the particular well of multiwell titerplate 92 may be a coverglass 160. This coverglass may rest on the top of the fluid and microtiter well 92. The use of a coverglass 160 may avoid the formation of the fluid meniscus at the top of the column of fluid in the particular well of multiwell titerplate 92. Menisci forming at the air/liquid boundary may have a dome shape that can interfere with the direct transmission of light there through, and therefore with the imaging of the biological specimen 140.

The container containing at the least one biological sample with the fluorescent dye may by covered with a transparent or semitransparent cover plate. A transparent or semitransparent cover plate may be, for example, a coverglass which either transparent or provided with a coating transparent for fluorescence signals but reflective for quenching radiation. As shown in FIG. 7, radiation from optical source 62 may pass through objective lens 64 and into the biological specimen 140 submerged in buffer fluid 150, it may travel through the two transparent surfaces 170, through the specimen, and through the optical coverglass 160. At this point, the radiation may impinge upon optical reflector 69. Optical reflector 69 may be disposed above the microtiter well 92, and oriented such that the reflection is not directly anti-parallel to the incoming radiation, but instead has an angular offset such that the reflection travels laterally buy some distance until impinging upon a second optical reflector 69'. Once again the radiation is reflected from optical reflector 69' back to optical reflector 69. With each pass, the radiation also travels some distance laterally. Accordingly, multiple passes of the radiation through the specimen are achieved, before either a lateral barrier is encountered or the radiation is extinguished or absorbed. As with the double pass described above, these multiple passes may enhance the effectiveness of the quenching operation on the fluorescent tag affixed to the biological specimen 140, and complete quenching of the fluorescent light may be achieved.

Figure 8:
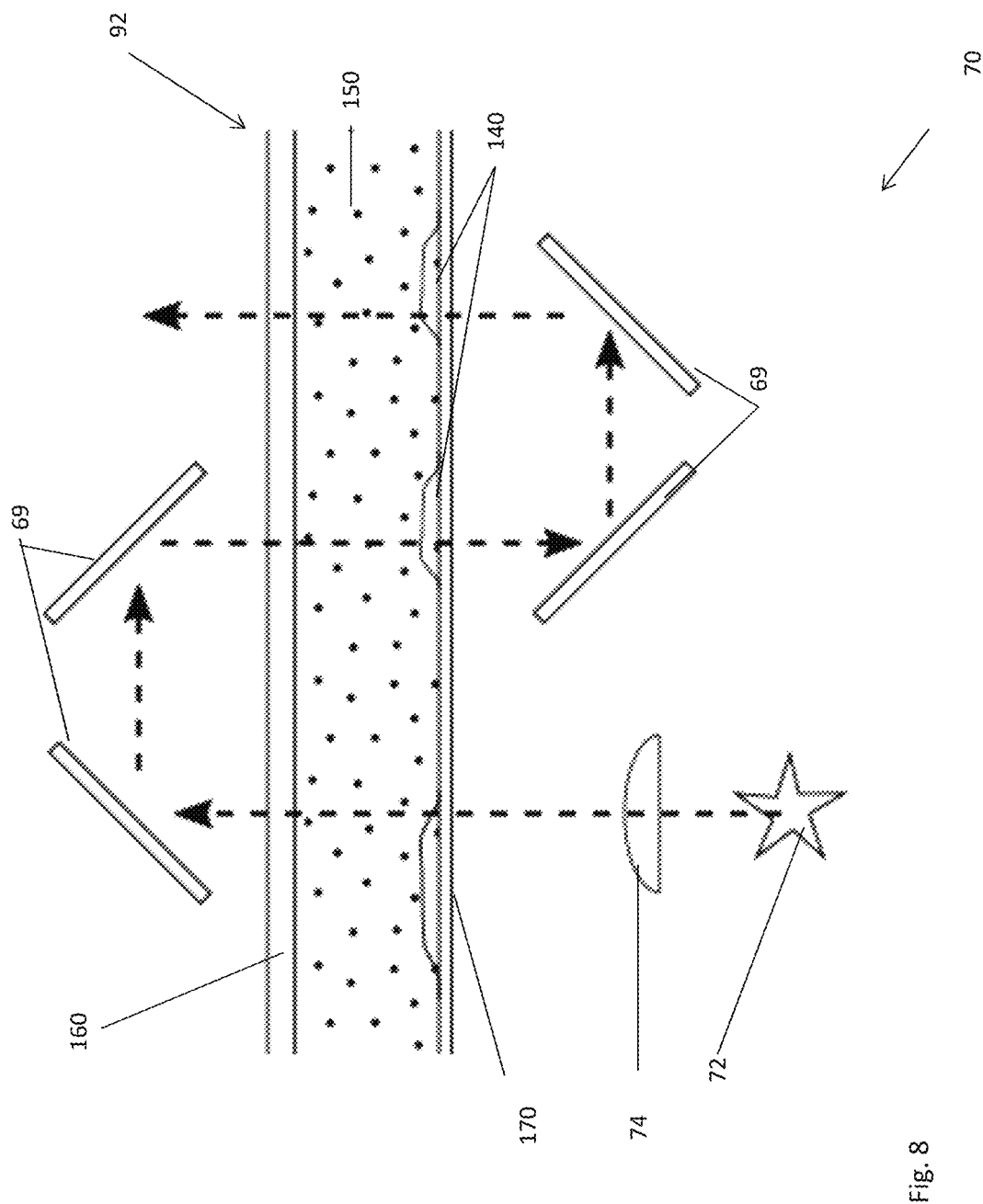
FIG. 8 is a simplified side view of another embodiment of an optical quenching system with multiple passes through the biological sample.

FIG. 8 is a conceptual side view of another embodiment of the optical quenching system 70. As in optical quenching system 60, a source of radiation 72 is focused through an objective lens 74 and into the disposable 92, which may be a multiwell titerplate or glass side. Optical source 72 may be either a light emitting diode (LED 42 as in FIG. 4) or laser (Laser source 52 as in FIG. 5). When entering the disposable 92, the radiation may pass through a transparent, glass base support 170 of disposable 92. This transparent base 170 may support a biological specimen 140. Biological specimen 140 may be at the bottom of particular well of disposable 92, but submerged in a fluid such as a buffer fluid 150. As in FIG. 7, at the top of the particular well of disposable 92 may be a coverglass 160. This coverglass may rest on the top of the fluid and disposable 92.

As with the previous embodiment, radiation from optical source 72 may pass through objective lens 74 and into the biological specimen 140 submerged in buffer fluid 150. Accordingly, the radiation may travel through the two transparent surfaces 170, through the specimen, and through the optical coverglass 160. At this point, the radiation may impinge upon optical reflector 69. Optical reflector 69 may be disposed above the microtiter well 92, and angled with respect to surfaces 160 and 170. In this way, light from light source 72 may be reflected laterally by some distance, impinging on another reflector 69. This reflector is disposed in an opposite sense, such that the horizontally traveling radiation is reflected in the vertical direction, and thus back through the transparent surfaces 160 and 170, and in a second pass back through the biological specimen 140. After the second pass, the radiation is reflected off the two optical reflectors 69' which may be identical to optical reflectors 69, but disposed underneath and laterally adjacent to optical reflectors 69. The radiation is once again reflected sideways and back through the biological specimen 140. With each pass, the radiation also travels some distance laterally. Accordingly, multiple passes of the radiation through the specimen are achieved, before either a lateral barrier is encountered or the radiation is extinguished or absorbed. As with the double pass described above, these multiple passes may enhance the effectiveness of the quenching operation on the fluorescent tag affixed to the biological specimen 140, and complete quenching of the fluorescent light may be achieved. Accordingly, as described above, multiple mirrors may be used for creating a system generating many passes of the quenching light through the sample, like a Herriott-type or a White-type multi-reflection cell or a resonator.

While four reflectors (69 and 69') are shown in FIG. 8, it should be understood that the concepts described here can be extended to any number of reflectors and passes.

Figure 9:
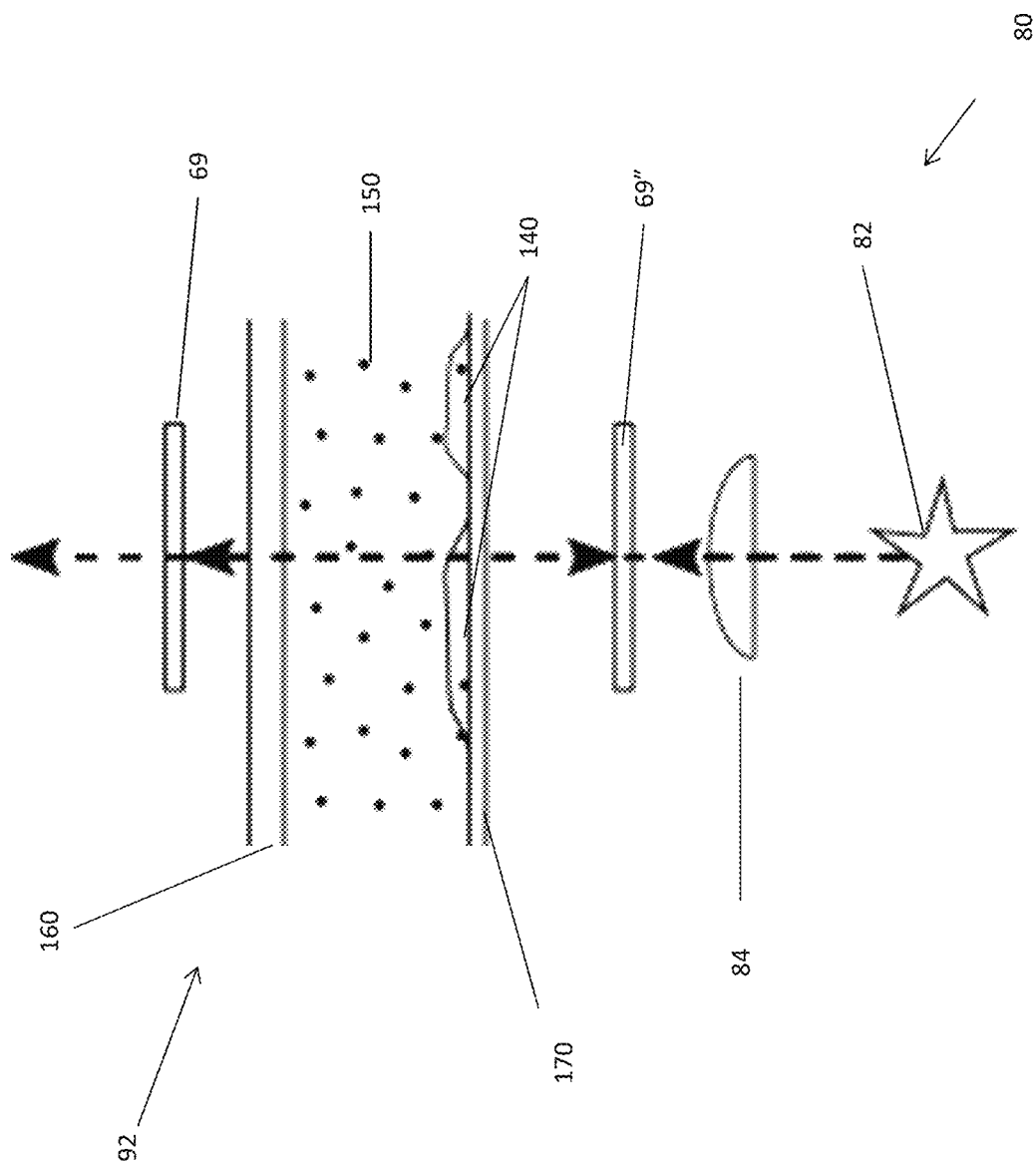
FIG. 9 is a simplified side view of another embodiment of an optical quenching system with multiple passes through the biological sample.

FIG. 9 is a conceptual side view of another embodiment of the optical quenching system 80. As in optical quenching system 60 and 70, a source of radiation 82 is focused through an objective lens 84 and into the multiwell titerplate 92. Optical source 82 may be either a light emitting diode (LED 42 as in FIG. 4) or laser (Laser source 52 as in FIG. 5). When entering the multiwell titerplate 92, the radiation may pass through a transparent, glass base support 170 of multiwell titerplate 92. This transparent base 170 may support a biological specimen 140. Biological specimen 140 may be at the bottom of particular well of multiwell titerplate 92, but submerged in a fluid such as a buffer fluid 150. At the top of the particular well of multiwell titerplate 90 may be a coverglass 160. This coverglass 160 may rest on the top of the fluid and microtiter well 92.

As with the previous embodiment, radiation from optical source 82 may pass objective lens 84 and through partially transmitting surface 69, into the biological specimen 140 submerged in buffer fluid 150. As before, the radiation may then travel through the transparent surface 170, through the specimen, and through the optical coverglass 160. At this point, the radiation may impinge upon a second partially transmitting optical reflector 69". Optical reflector 69" may be disposed above the microtiter well 92, orthogonal to the path of the radiation and parallel to optical reflector 69. Because both optical reflectors 69 and 69" are partially reflecting and partially transmitting, they may form an optical resonator when used in conjunction with a coherent radiation source such as laser 82. Accordingly, fine adjustments in the location of reflector 69" with respect to reflector 69 may have a dramatic effect on the amount of radiation circulating within the resonator, and thus on the quenching effectiveness of the fluorescent quenching system 80. Accordingly, multiple passes of the radiation through the specimen are achieved, before either the photon exits the resonator through end reflector 69 or the photon is extinguished or absorbed. As with the double pass described above, these multiple passes may enhance the effectiveness of the quenching operation on the fluorescent tag affixed to the biological specimen 140, and complete quenching of the fluorescent light may be achieved.

Accordingly, the optical quenching system may further comprise a laser light source and two mirrors above and below the disposable, which define a resonant cavity for the laser light source.

It should be understood that any and all of these embodiments may also be coupled with a florescence detector and computer as described with respect to the embodiment illustrated in FIG. 5. Accordingly, the optical source 42, 52, 62, 72 and 82 may be under feedback control until the complete quenching of the fluorescence signal is achieved.

Figure 10:
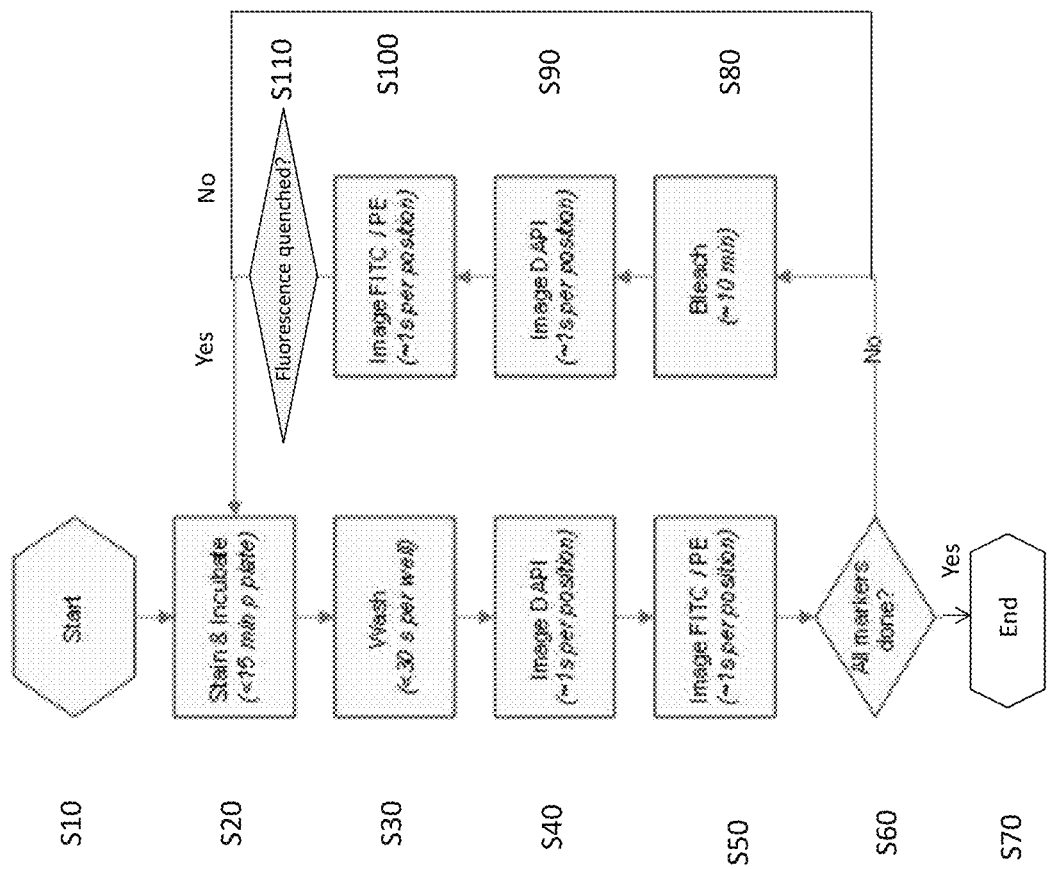
FIG. 10 is a simplified flow chart showing a method for using the automated tool for biological specimens.

Having described the components of exemplary fluorescence imaging systems 30 and exemplary fluorescence quenching systems 40, a method of using the apparatus will be described next. It should be understood that this method may make use of any and all of the components in the previously described embodiments. The method in general will be outlined below, followed by a specific algorithm as illustrated in FIG. 10.

In general, a plurality of biological samples held in microtiter plate 92 are stained with one of the reagents held in microtiter plate 90. By positioning the appropriate fluid well of microtiter plate 90 under the pipetting 70, the reagent may be withdrawn by applying suction to the pipette 70. The reagent is then delivered to the appropriate biological sample by shifting the x-y stage laterally until the proper well is under pipette 70. The reagent is delivered to the biological sample.

After incubation, the sample may be imaged by the fluorescent imaging system 30 by moving movable x-y stage to bring the sample into the field of view of the fluorescence imaging system 30. The x-y working plane is then shifted laterally, such that the biological sample is placed in the illuminated region of the fluorescence quenching system 40. The fluorescence is then quenched by optical radiation, oxidation or enzymatical degradation and subsequent washing. After adequate quenching, optionally the sample is imaged for correction/control purposes and then another reagent is applied to the sample, and the process is repeated. This sequence of steps can be repeated until a large number of reagents has been applied to the at least one biological sample.

It should be understood that additional steps such as adding buffer, washing, adding or withdrawing fluid, chilling and heating may be added as appropriate.

FIG. 10 is a simplified flow chart of a particular method for using the automated analysis tool for analysis of biological specimens described above with respect to FIGS. 1-9. The method begins in step S10 and continues to step S20. In step S20, the specimen is stained with at least one fluorescent reagent and incubated. In this embodiment, DAPI is applied followed by two fluorescent reagents such as, FITC and PE. During incubation, the reagents may be taken up by the biological specimen. In step S30, the specimen is washed. In this step, additional buffer may be added to the well by pipette. The excess fluid is subsequently withdrawn by pipette. In step S40, the specimen is then positioned over the fluorescence imaging system, and the DAPI image is obtained. This image may identify prominent structures in the specimen such as the nucleus, mitochondria, etc. These prominent structures may serve as landmarks, in order to allow the imaging system to position the sample in the exact same location, after relocating the disposable between the imaging and quenching steps.

The fluorescent imaging system may then be configured to image FITC and PE fluorescence in step S50. The image acquired under these conditions may be indicative of the binding of the specimen with the antibodies conjugated to the FITC or PE fluorophores. In subsequent step S60, the question of whether all markers have been imaged is asked. If so, the process ends in step S70. If additional markers remain, the specimen is bleached or quenched of fluorescence in step S80. This bleaching step may be accompanied by the mechanical shifting of the disposable laterally such that the sample is positioned over the quenching system.

Accordingly, the routine may include the quenching of a fluorescence signal by the quenching system between the application of different compounds. The sample may be repositioned by locating the previously identified features or landmarks under computer control. The computer may move the working plane such that the same features are displayed in repeated applications of the different compounds, rendering a comparative view of the biological sample and its interaction with the different applied compounds.

The DAPI is then imaged again to re-locate the sample with respect to the images taken in step S40, and the fluorescence image of FITC and PE is again taken. If the fluorescence has been quenched or extinguished, the method returns to step S20 wherein a new stain is applied and the sample is incubated.

In a variant of the invention re-location of the sample may be achieved not by DAPI staining of the sample but by providing the container containing the sample with a particle/spot or dot of a fluorescence marker. This variant is especially useful when the sample are isolated cells in microcavities.

Also shown in the flowchart of FIG. 9 is the loop wherein the fluorescence has not been completely quenched, and the loop is repeated. This method corresponds most closely with the embodiment shown in FIG. 4, with the fluorescent quenching system 40 under feedback control. In step S110, the fluorescence is measured to see if it has fallen below a threshold level. If so, the process returns to step S20. If not, the quenching process is repeated in step S80.

More generally, the automated method may include holding at least one biological sample with the fluorescent dye in a container in an aperture on a stage, exciting the fluorescent dye and imaging the fluorescence signals obtained from the fluorescent dye with a fluorescence system, moving at least one of the aperture, the stage, the fluorescence system, and a quenching unit in at least two orthogonal dimensions that define a working plane until the biological sample is adjacent to a quenching unit, quenching the fluorescence signal with the quenching unit, and imaging the biological a sample after the quenching. The automated method may further comprise transferring a sequence of fluids with a fluid handling system into the container holding the biological sample, and executing a routine including excitation of the fluorescent dye, detection and collection of the fluorescence signals and quenching of the fluorescence signals in an automated fashion with the sequence of fluids.

Accordingly, disclosed here is an automated system for analyzing biological samples stained with at least one fluorescent dye. The system may include a stage movable laterally in the x- and y-direction for holding at least one biological sample stained with the fluorescent dye, a detector for detecting the fluorescence signals obtained from the fluorescent dye on the biological sample in a field of view of the detector, and a fluorescence system including a light source producing a first radiation which excites the fluorescent dye on the biological sample by impinging its radiation on the field of view. As used herein, the term "field of view" should be understood to mean the lateral extent or field from which an emitted optical ray can pass through the aperture and impinge on the sensor area of a detector. In other words, the field of view is the solid angle through which a detector is sensitive to electromagnetic radiation.

The system may further include a controller executing a routine that moves the biological sample by shifting the biological sample laterally on the movable stage to the field of view of the detector, and wherein the controller directs the light source to produce a second radiation which quenches the fluorescence signals obtained from at least a part of the sample, after detection by the detector. As used herein, the term "executing a routine" should be understood to refer to the performing of a set of microprocessor instructions by a microprocessor to accomplish a given task. These instructions may be stored on a computer-readable medium such as magnetic disk storage, flash RAM or optical disk.

The automated system may further comprise a fluid handling system providing at least one of fluorescence dyes, compounds quenching the fluorescence signals, and washing fluids and buffer to the biological sample. The controller may collect the fluorescence signals from the detector as images of the biological sample stained with a fluorescence dye. The fluid handling system may include a robotically controlled pipette system disposed on a stage, wherein the pipetting system is movable along a z-axis orthogonal to the working plane. The fluid handling system may further include at least one additional fluid vessel containing at least one of reagents, antigen recognizing moieties having detection moieties, antibodies with fluorescent dyes, antibiotics, biological nutrients, toxins, stains, and oxidants. The fluid handling system may further comprise a container with a plurality of fluid wells, each containing a separate biological sample, wherein the container is a titer plate. The container may further comprise transparent and nontransparent parts wherein the biological sample is located on the transparent part and the nontransparent parts either reflect or absorb the fluorescence signals.

Within the automated system, the second radiation may be produced by a light emitting diode. large enough to illuminate more than one field of view. The automated system may further include at least one mirror which reflects a part of the second radiation which is not absorbed by the biological sample or the fluorescent dye back into the biological sample. The fluorescence system may further include a fluorescence detector which monitors decay of the fluorescence signal as quenching data. The controller is configured to control intensity and duration of the second radiation with a feedback loop based on the quenching data. The controller may be configured to move the biological sample on the movable stage with a precision of +/− about 1-200 microns in x or y direction. The automated system may further include a temperate control unit that controls the temperature of the biological sample to 10-40° C.

The detector may detect fluorescence signals obtained from the fluorescent dye in field of view, wherein the field of view is a portion of the biological sample that can be viewed by the detector when motionless. The controller may be configure to move the detector over the biological sample until the detector detects all fluorescence signals obtained from the fluorescent dye of the entire biological sample, by shifting sequentially the field of view of the detector over the entire biological sample, by shifting at least one of the detector and the biological sample. The controller may also be configured to move the excitation unit, the detector and the fluorescence system over the biological sample until the detector detects all fluorescence signals obtained from the fluorescent dye of all parts of the biological sample wherein quenching of the fluorescence signals is performed for each of the areas of the biological sample after detection the fluorescence signals.

The controller may be configured to quench fluorescence signals of the biological sample after all fluorescence signals are detected from all parts (area) of the biological sample.

Also disclosed is an automated method for analyzing biological samples. The method may include holding at least one biological sample with the fluorescent dye in a container, irradiating the biological sample with the fluorescent dye with a first radiation from a fluorescence system, detecting the fluorescence signals obtained from the fluorescent dye with a detector having a field of view, quenching the fluorescence signal with a second radiation from the fluorescence system, after detection of the fluorescence signal, and moving at least one of the field of view, the stage, the fluorescence system, and the biological sample in at least two orthogonal dimensions that define a working plane, until a new field of view of the biological sample is adjacent to the fluorescence system.

The automated method may further include imaging the biological a sample after the quenching. The method may also include transferring a sequence of fluids with a fluid handling system into the container holding the biological sample, and executing a routine including excitation of the fluorescent dye, detection and collection of the fluorescence signals and quenching of the fluorescence signals in an automated fashion with the sequence of fluids.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, details related to the specific methods, dimensions, materials uses, shapes, fabrication techniques, etc. are intended to be illustrative only, and the invention is not limited to such embodiments. Descriptors such as top, bottom, left, right, back front, etc. are arbitrary, as it should be understood that the systems and methods may be performed in any orientation. Accordingly, the exemplary implementations set forth above, are intended to be illustrative, not limiting.

What is claimed is:

1. An automated system for analyzing biological samples stained with at least one fluorescent dye, comprising:
   at least one biological sample stained with a fluorescent dye;
   a first stage movable laterally in the x- and y- direction for holding the at least one biological sample, wherein the at least one biological sample is stained with the fluorescent dye, this lateral x- y- direction defining a working plane and which holds the at least one biological sample in a first position;
   a fluorescence system including at least one light source producing a first radiation and wherein the first radiation excites the fluorescent dye on the at least one biological sample;
   a quenching system including a second light source, which diminishes the first fluorescence signals by application of a second radiation produced by the second light source;
   and wherein a fluorescence detector detects first fluorescence signals obtained from the fluorescent dye on the at least one biological sample in a field of view of the fluorescence detector and monitors decay of the fluorescence signal from the at least one biological sample as quenching data, and
   a computer readable medium with a non-transitory memory, wherein the non-transitory memory is encoded with instructions for a controller to move the stage laterally to the first position; apply the first radiation to the at least one biological sample; measure the first fluorescence signals; apply the second radiation, and measure a diminution of the first fluorescent signals to generate quenching data, and to adjust duration and intensity of the second radiation with a feedback loop using the quenching data, and to store the quenching data related to the first position.

2. The automated system of claim 1, further comprising a fluid handling system operatively coupled to the first stage for providing biologically active compounds to the at least one biological sample, wherein the biologically active compounds comprise at least one of fluorescence dyes, compounds quenching the fluorescence signals, and washing fluids and buffer, wherein the fluid handling system transfers these biologically active compounds to the at least one biological sample.

3. The automated system of claim 1, wherein the controller collects the fluorescence signals from the detector as images of the at least one biological sample stained with a fluorescence dye.

4. The automated system of claim 2, wherein the fluid handling system comprises a robotically controlled pipette system disposed on a second stage, wherein the pipetting system and second stage is movable along a z-axis orthogonal to the working plane of the detector, and supplies the at least one biological sample to the sample stage.

5. The automated system of claim 2, wherein the fluid handling system comprises at least one additional fluid vessel containing said biologically active compounds, said biologically active compound comprising at least one of reagents, antigen recognizing moieties having detection moieties, antibodies with fluorescent dyes, antibiotics, biological nutrients, toxins, stains, and oxidants.

6. The automated system of claim 1, wherein the first stage further comprises a container for holding the at least one biological sample, the container having a plurality of fluid wells, each containing a separate biological sample, wherein the container for holding the at least one biological sample is a titer plate.

7. The automated system of claim 6, wherein the container comprises transparent and nontransparent parts wherein the at least one biological sample with fluorescent dye is located on the transparent part and the nontransparent parts either reflect or absorb the fluorescence signals, wherein the transparent part allows the passage of the first and second radiation.

8. The automated system of claim 1, wherein the second radiation is produced by a light emitting diode with a beam angle, and wherein the light emitting diode is disposed to illuminate the at least one biological sample beyond the field of view of the detector.

9. The automated system of claim 8, further comprising at least one mirror disposed to reflect a part of the second radiation produced by the light emitting diode, which is not absorbed by the at least one biological sample or the fluorescent dye, back into the at least one biological sample, to quench the fluorescence.

10. The automated system of claim 1, wherein the controller is configured to control intensity and duration of the second radiation to diminish the first fluorescence signals until the first fluorescence signals reach a predefined level, and the controller stores the first fluorescence signals and quenching data as relating to the first position in an image.

11. The automated system of claim 1, wherein the controller moves the at least one biological sample on the movable stage with a precision of +/− about 1-200 microns in x or y direction.

12. The automated system of claim 1, further comprising an enclosure surrounding the at least one biological sample, along with a temperate control unit which maintains the temperature of the at least one biological sample in the enclosure to 10-40° C. by chilling or heating the enclosure of the at least one biological sample.

13. The automated system of claim 1, wherein the fluorescence detector detects fluorescence signals obtained from the fluorescent dye in field of view, wherein the field of view is a portion of the at least one biological sample that can be viewed by the detector when motionless.

14. The automated system of claim 10, wherein after obtaining the first data relating to the first position in an image, the controller is configured to move the first stage holding the at least one biological sample in the first position relative to the detector to a second position relative to the detector, to obtain second data relating to the second position, and constructs fluorescent image including the first and the second data until the detector detects all fluorescence signals obtained from the fluorescent dye over an entirety of the at least one biological sample, by comparing detector/sample relative locations to known locations of the at least one biological sample.

15. The automated system of claim 1, wherein the controller is configured to execute a method of moving the first stage to a plurality of points on the at least one biological sample and repeats collection of data at each of the plurality of points until the data includes an entire region of interest in the at least one biological sample, and the controller processes the data to form an image of the at least one biological sample.

16. The automated system of claim 1, wherein the controller is configured to quench fluorescence signals by increasing or continuing the radiation applied to the biological specimen until the fluorescence signal ceases to be emitted from the at least one biological sample as detected by the fluorescence detector.

* * * * *